US00PP33901P2

(12) United States Plant Patent
Grazzini

(10) Patent No.: US PP33,901 P2
(45) Date of Patent: Jan. 25, 2022

(54) ***DIANTHUS* PLANT NAMED 'G18139'**

(50) Latin Name: *Dianthus hybrida*
Varietal Denomination: G18139

(71) Applicant: Garden Genetics, Bellefonte, PA (US)

(72) Inventor: Richard A. Grazzini, Bellefonte, PA (US)

(73) Assignee: Garden Genetics llc, Bellefonte, PA (US)

( * ) Notice: Subject to any disclaimer, the term of this patent is extended or adjusted under 35 U.S.C. 154(b) by 0 days.

(21) Appl. No.: 17/354,170

(22) Filed: Jun. 22, 2021

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273
CPC ..... A01H 6/305; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Dianthus* plant named 'G18139' is disclosed, characterized by rose-colored flowers with a distinct white eye. Plants are Winter hardy in Zone 5 and flower continuously from May through early November at 41N latitude. Healthy plants and leaves with constant growth from center. The new variety is a *Dianthus*, normally used for outdoor ornamental purposes.

2 Drawing Sheets

Figure 1:
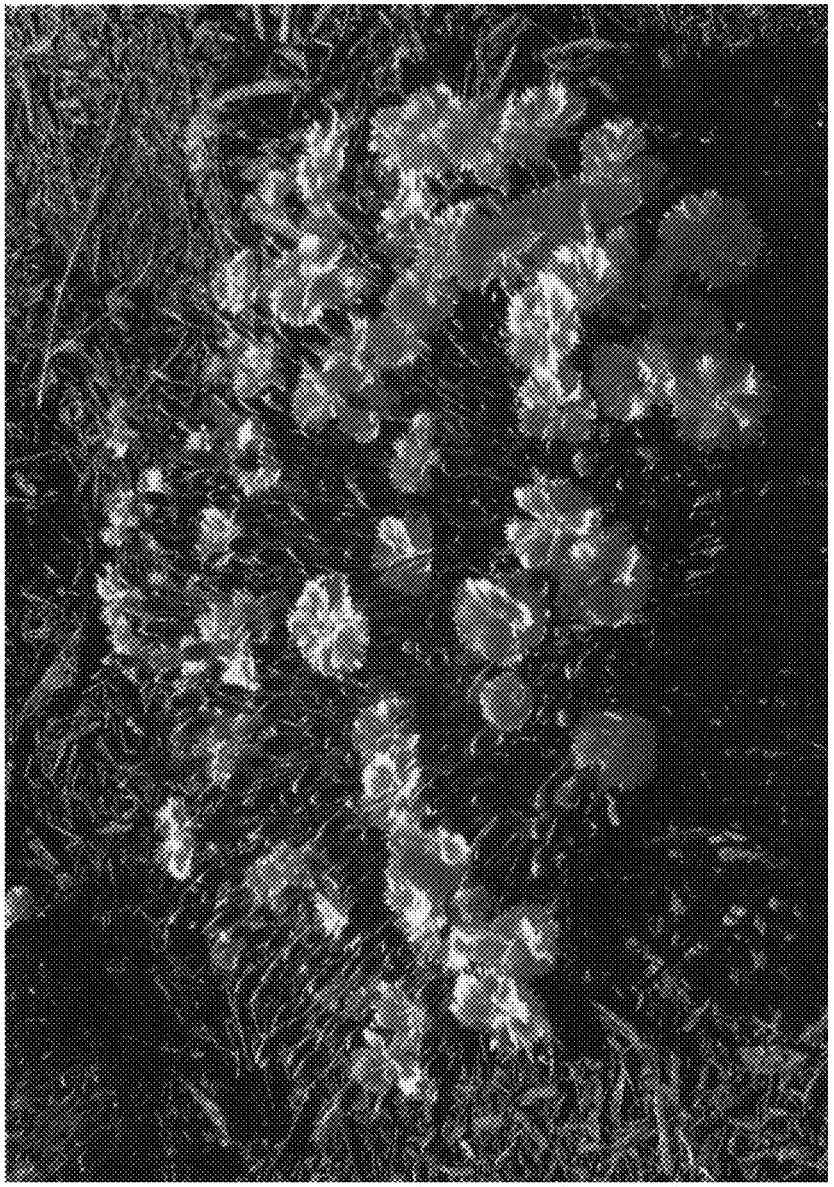

Latin name of the genus and species: *Dianthus hybrida.* Variety denomination: 'G18139'.

BACKGROUND OF THE INVENTION

The new *Dianthus* cultivar is a product of a planned breeding program conducted by the inventor at a research nursery in Bellefonte, Pa. The cross resulting in this new variety was made in December of 2017.

The seed parent is the unpatented proprietary variety referred to as *Dianthus* 'G17-018'. The pollen parent is the unpatented proprietary variety referred to as *Dianthus* 'G17-024'. The new variety was selected in June of 2018 by the inventor in a group of seedlings resulting from the 2017 cross-pollination, in a nursery in Bellefonte, Pa.

Asexual reproduction of the new cultivar was performed by vegetative cuttings. This was first performed at the same nursery in in Bellefonte, Pa. during July of 2018, and has shown that the unique features of this cultivar are stable and reproduced true to type in multiple successive generations.

SUMMARY OF THE INVENTION

The cultivar 'G18139' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G18139' These characteristics in combination distinguish 'G18139' as a new and distinct *Dianthus* cultivar:

1. Flowers are mid-rose in color, with a distinct white eye, and a slightly variable white picotee edge.
2. Flowers continuously in a greenhouse under ambient (natural) lighting.

3. Flowers constantly outdoors (in-ground) from late May through early November at 41N latitude.
4. Large flowers on short peduncles, forming a dense floral canopy just above the foliage.
5. Good winter-hardiness (USDA z5, at least) and good winter survival.
6. Healthy plants and leaves with constant growth from center (does not form "donut" or "birds' nest").
7. Strong field-tolerance to common *Dianthus* pathogens.

PARENT COMPARISON

Plants of the new cultivar 'G18139' are similar to plants of the seed parent in most horticultural characteristics; however, plants of the new cultivar 'G18139' differ in the following:

1. New variety 'G18139' has rose-pink flowers with a white "eye", and a slight white picotee flower edge. Seed parent 'G17-018' has light pink flowers with a dark violet eye.
2. New variety 'G18139' has grey-green foliage. Seed parent 'G17-018' has silvery-blue leaves.
3. New variety 'G18139' has relatively short peduncles. Seed parent 'G17-018' has much longer peduncles.
4. New variety 'G18139' flowers continuously under natural light at 41N latitude. Seed parent 'G17-018' repeat-blooms, cycling in and out of flower.
5. New variety 'G18139' is field-tolerant of *Dianthus* leaf and crown pathogens. Seed parent 'G17-018' is not tolerant, and typically dies out in the center, forming a "donut" of healthy foliage around a dead center.

Plants of the new cultivar 'G18139' are similar to plants of the pollen parent in most horticultural characteristics; however, plants of the new cultivar 'G18139' differ in the following:

1. New variety 'G18139' has rose-pink flowers with a white "eye", and a slight white picotee flower edge. Pollen parent 'G17-024' has light pink flowers and no eye.
2. New variety 'G18139' has grey-green foliage. Pollen parent 'G17-024' has medium-green leaves.
3. New variety 'G18139' has short peduncles. Pollen parent 'G17-024' has much shorter peduncles, so that the flowers are very close to the foliage.
4. New variety 'G18139' flowers continuously under natural light at 41N latitude. Pollen parent 'G17-024' repeat-blooms, cycling in and out of flower.
5. New variety 'G18139' is field-tolerant of *Dianthus* leaf and crown pathogens. Pollen parent 'G17-024' is not especially tolerant, and typically dies out in the center, forming a "donut" of healthy foliage around a dead center.

COMMERCIAL COMPARISON

Plants of the new cultivar 'G18139' are comparable to the commercial variety *Dianthus* 'Devon Esther', U.S. Plant Pat. No. 18,222. The two *Dianthus* varieties are similar in most horticultural characteristics, however, the new variety 'G18139' differs in the following:

1. New variety 'G18139' is single-flowered. Comparison variety 'Devon Esther' is double- flowered.
2. New variety 'G18139' flowers continuously under natural light at 41N latitude. Comparison variety 'Devon Esther' repeat-blooms under similar conditions.
3. New variety 'G18139' has grey-green foliage. Comparison variety 'Devon Esther' has silvery- blue leaves.
4. New variety 'G18139' has rose-pink flowers with a white "eye", and a slight white picotee flower edge. Comparison variety 'Devon Esther' has lavender-rose flowers with a violet eye.
5. New variety 'G18139' is more compact, with shorter flower peduncles. Comparison variety 'Devon Esther' is taller with longer flower peduncles.

Plants of the new cultivar 'G18139' are comparable to the commercial variety *Dianthus* 'Uribest52', U.S. Plant Pat. No. 28,239. The two *Dianthus* varieties are similar in most horticultural characteristics; however, the new variety 'G18139' differs in the following:

1. New variety 'G18139' has bright-rose pink flowers. Comparison variety 'Uribest52' has deep red-purple flowers.
2. Flowers of variety 'G18139' have a white eye, and a slight white picotee edge. Comparison variety 'Uribest52' has no eye in its flowers.
3. New variety 'G18139' has large single flowers. Comparison variety 'Uribest52' has relatively small flowers in comparison.
4. New variety 'G18139' has longer peduncles. Comparison variety 'Uribest52' has shorter peduncles.
5. New variety 'G18139' has grey-green foliage. Comparison variety 'Uribest52' has mid-green foliage.

BRIEF DESCRIPTION OF THE PHOTOGRAPHS

The accompanying photograph in FIG. 1 illustrates a typical flowering plant of 'G18139' grown outdoors in Bellefonte, Pa. at approximately 4 months old in a 1-gallon pot.

Figure 2:
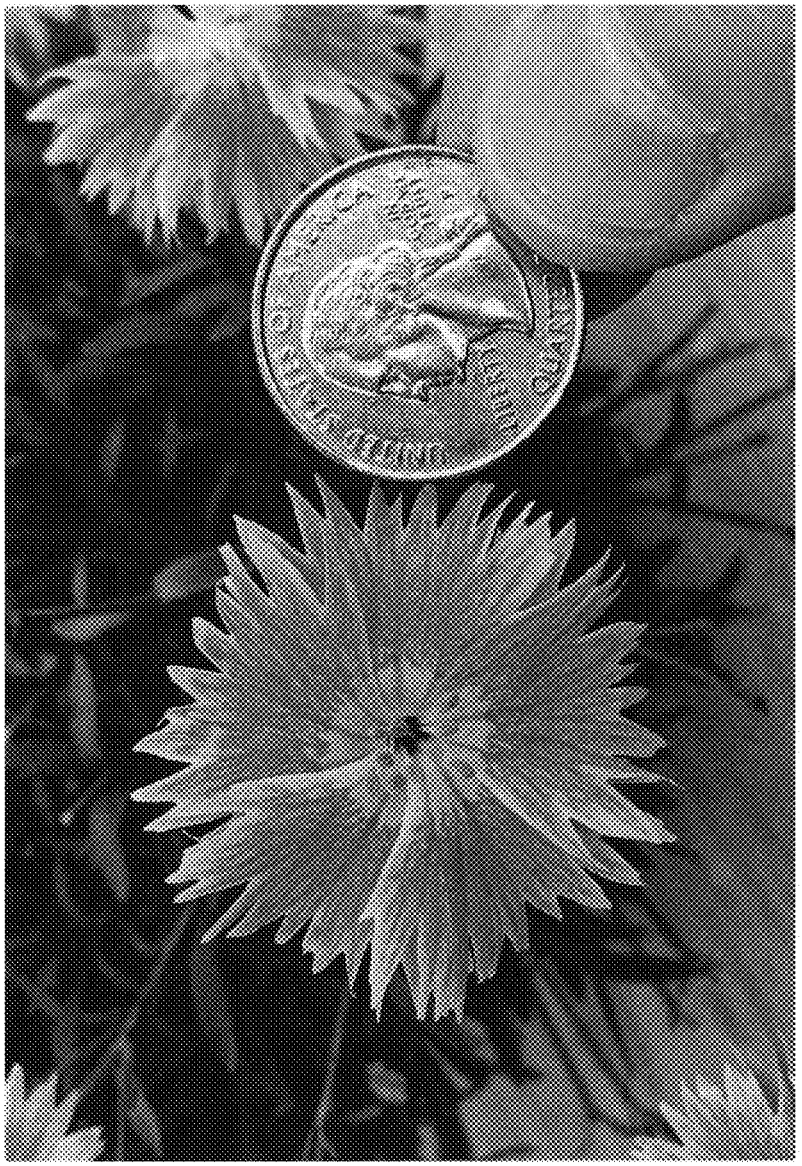

FIG. 2 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'G18139' plants grown outdoors in Camarillo, Calif. The growing temperature ranged from approximately 10° C. to 25° C. during the day and from approximately 6° C. to 12° C. during the night. General light conditions are normal sunlight and numerical values represent averages of typical plant types. Measurements were taken during June of 2021.

Botanical classification: *Dianthus hybrida* 'G18139'.

PROPAGATION

Time to initiate roots: About 10 days at approximately 24° C.

Time to produce a rooted cutting: About 18 days at 24° C.

Root description: Fibrous roots, approximately 1 to 3 mm in diameter, colored near RHS Orange-White 159C.

PLANT

Age of plant described: About 10 weeks from a rooted cutting.

Growth habit: Mounded flowering perennial.

Plant spread: About 21 cm.

Plant height: About 9 cm.

Plant vigor: Strong.

Length plant stem: Average 7 cm.

Diameter of plant stem: Approximately 3 mm.

Quantity stems: Approximately 30 to 40.

Stem:

*Color.*—Near RHS Greyed-Green 191C.

*Texture.*—Smooth.

*Hollowness.*—Slightly hollow with age.

Internode length: 1 to 2 cm.

FOLIAGE

Leaf:

*Arrangement.*—Opposite (in pairs).

*Quantity.*—Approximately 10 to 14 fully expanded per stem.

*Average length.*—2.5 to 4.3 cm.

*Average width.*—3 to 4 mm.

*Shape of blade.*—Linear.

*Apex.*—Acute.

*Base.*—Clasping.

*Attachment.*—Sessile.

*Margin.*—Entire.

*Texture of top surface.*—Smooth.

*Texture of bottom surface.*—Smooth.

*Pubescence.*—None.

*Color.*—Young foliage upper side: Near RHS Green N138A. Young foliage under side: Near RHS Green N138B. Mature foliage upper side: Near RHS Green N138A. Mature foliage under side: Near RHS Green N138C.

*Venation*.—Type: Linear. Venation color upper side: Indistinguishable from foliage. Venation color under side: Indistinguishable from foliage.

FLOWER

Natural flowering season: May through early November at 41N latitude.
Inflorescence type and habit: Umbel of 2 to 4 flowers.
Flower longevity on plant: Individual flowers about 10 days.
Quantity of flowers: Approximately 50 flowers and buds on a 10-week-old plant.
Flowers persistent or self-cleaning: Persistent.
Fragrance: Faint sweet scent.
Inflorescence (umbel) size:
*Diameter*.—Approximately 6.0 cm.
*Height*.—Approximately 5.0 cm.
Individual flower size:
*Diameter*.—Approximately 2.7 cm.
*Length*.—Approximately 2.5 cm.
Petals:
*Petal arrangement*.—Single overlapping whorl.
*Shape*.—Spatulate, elongated base.
*Base*.—Long attenuate.
*Margin*.—Serrated.
*Apex*.—Serrate.
*Length*.—Upper section, outside of tube: 1.3 cm. Elongated base, in tube, 1.6 cm.
*Width*.—Upper section, outside of tube: 1.3 cm. Elongated base, in tube, 3 mm.
*Petal quantity*.—Average range 15 to 18.
*Texture*.—Smooth all surfaces.
*Aspect*.—Nearly flat.
Color:
*When opening*.—Upper surface: Near RHS Red-Purple N74A, streaked Red-Purple 70C, margins near Purple 75B. Center eye Red-Purple N74D. Lower surface: Near RHS Red-Purple N74B streaked Red-Purple N74C. Base near tube N74D.
*Fully opened*.—Upper surface: Near RHS Red-Purple N74B, streaked Red-Purple 70D, margins near Purple 75C. Center eye Red-Purple 70D. Lower surface: Near RHS Red-Purple N74C streaked Purple 75C. Base near tube N74D.
Tube:
*General description*.—Tube consists of the elongated, unfused base of the petals. Tube shape caused by a fused calyx.
*Length*.—1.7 cm.
*Width*.—5 mm.
*Texture*.—Smooth.
Color:
*Fully opened*.—Inner surface: Near RHS Green N138D. Outer surface: Near RHS Green N138D.
Bud:
*Shape*.—Elongated cylinder.
*Length*.—Average 1.8 cm.
*Diameter*.—Average 0.9 cm.
*Color*.—Appearing petals colored near RHS Red-Purple N74B.
Sepals:
*Quantity*.—5.
*Arrangement*.—Fused tube.
*Shape*.—Cylindric.
*Length*.—1.3 cm.
*Width*.—0.3 cm.
*Margin*.—Entire.
*Apex*.—Acute.
*Texture*.—Smooth upper and lower surfaces.
*Color*.—Near RHS Green N138D.
Bracteoles:
*Shape*.—Narrow deltoid.
*Quantity per flower*.—5-7.
*Length*.—Average 5 mm.
*Width*.—Average 4 mm.
*Margin*.—Entire.
*Texture*.—Smooth.
*Color*.—Near RHS Green N138D.
Peduncle:
*Length*.—Average 3 to 4 cm.
*Diameter*.—2.0 mm.
*Color*.—Near RHS Green N138D.
*Orientation*.—Upright.
*Strength*.—Moderate.
*Texture*.—Smooth.

REPRODUCTIVE ORGANS

Stamens:
*Number*.—About 10.
*Filament length*.—1.5 cm.
*Filament color*.—Near RHS Red-Purple 69C.
Anthers:
*Shape*.—Linear.
*Length*.—3 mm.
*Color*.—RHS Greyed-Purple N187D.
*Pollen*.—Not observed.
Pistil:
*Number*.—1, 2 stigmas.
*Length*.—2.1 cm.
*Style*.—Number: 2. Length: Approximately 1.3 cm. Color: Base near RHS Red-Purple 69D, upper-section Red-Purple 69A.
*Stigma*.—Shape: Linear. Color: Near RHS Red-Purple 70D.
*Ovary*.—Shape: Oblong. Diameter: 7 mm. Length: 7 mm. Color: Near RHS Yellow-Green 150D.

OTHER CHARACTERISTICS

Fruits and seeds: Not observed to date.
Disease/pest resistance: Shows good field-tolerance to common *Dianthus* pathogens. Specific pathogens resistance has not been determined.
Temperature range: Winter hardiness to at least USDA Zone 5.

What is claimed is:

1. A new and distinct cultivar of *Dianthus* plant named 'G18139' as herein illustrated and described.

* * * * *